United States Patent [19]

Colacello et al.

[11] Patent Number: 5,658,267
[45] Date of Patent: Aug. 19, 1997

[54] COLOSTOMY COLLECTION POUCH WITH VENT VALVE

[76] Inventors: Michael Colacello, 543 Emmett Ave., Trenton, N.J. 08629; Albert Colacello, 4 Cranbrook Rd., Hamilton Square, N.J. 08690

[21] Appl. No.: 588,108

[22] Filed: Jan. 18, 1996

Related U.S. Application Data

[63] Continuation of Ser. No. 394,906, Feb. 27, 1995, abandoned, which is a continuation of Ser. No. 238,884, May 6, 1994, abandoned, which is a division of Ser. No. 100,370, Aug. 2, 1993, Pat. No. 5,372,594.

[51] Int. Cl.⁶ ............................................................. A61F 5/44
[52] U.S. Cl. ........................... 604/333; 604/327; 604/332; 604/335
[58] Field of Search ............................... 604/332–339, 604/340, 342, 327, 322; 137/318, 322; 220/367.1; 222/91

[56] References Cited

U.S. PATENT DOCUMENTS

| | | | |
|---|---|---|---|
| 2,573,424 | 10/1951 | Flamm | 137/318 |
| 4,322,018 | 3/1982 | Rutter | 222/83 |
| 4,516,974 | 5/1985 | Davis | 604/333 |
| 4,863,447 | 9/1989 | Smith | 604/335 |
| 5,303,732 | 4/1994 | Jonsson | 137/318 |

Primary Examiner—John G. Weiss
Assistant Examiner—Dennis Ruhl
Attorney, Agent, or Firm—Martin Sachs

[57] ABSTRACT

A manual gas vent assembly for use in venting gas from the interior of a conventional unvented ostomy collection pouch include a valve assembly having an open position, which permits gas to pass therethrough and a closed position, for preventing gas to pass therethrough. The valve assembly has an input portion for communicating with the interior of the ostomy collection pouch and an output portion for communicating with the atmosphere and a mounting device for mounting the valve assembly to a selected portion of the wall of the ostomy collection pouch. The mounting device releasably contains therein a portion of the valve assembly so as to position the input portion thereof proximate the interior of the ostomy collection pouch, and the output portion of the valve assembly proximate to the atmosphere. Also included is an absorbent pad suitable for receiving an antiseptic and/or deodorant.

11 Claims, 4 Drawing Sheets

COLOSTOMY COLLECTION POUCH WITH VENT VALVE

The present Application is a Continuation of application Ser. No. 08/394,906, filed Feb. 27, 1995, now abandoned which is a Continuation of application Ser. No. 08/238,884, filed May 6, 1994, by the Applicants Colacello, et al., now abandoned, which was a division of application Ser. No. 08/100,370 filed Aug. 2, 1993, now U.S. Pat. No. 5,372,594, issued Dec. 13, 1994.

BACKGROUND OF THE INVENTION

1. Field of the Invention

The present invention relates to ostomy collection pouches and more particularly to means for manually venting ostomy collection pouches into the surrounding atmosphere so that gas build up therein can be released.

2. Description of the Prior Art

A colostomy is a surgical procedure in which an artificial anus is formed to accommodate persons whose colon has become infected or cancerous and can no longer function. In such cases the patient is left with no normal bowel function and as a result of the colostomy, body wastes pass through the artificial anus into the colostomy collection bag.

A colostomy can be permanent or temporary but in either event the person must use a pouch system to collect bowel wastes. In some cases after the colon is healed, the surgical procedure is reversed for the temporary colostomy user, normal bowel function follows and the pouch is no longer needed. Unfortunately, permanent colostomy users need a pouch for the rest of their life to handle their body wastes.

Present day colostomy pouches are made of a plastic film. The top portion of the bag includes a hole with an adhesive substance surrounding the hole. This bag is attached to the persons body over the artificial anus and the waste is permitted to enter the pouch through the opening. The bottom part of the pouch may be fitted with a clamp assembly were the waste may be removed while the bag is still attached to the user's body.

Presently available pouches have been designed to serve this purpose well. The waste enters the pouch and is held by the clamp assembly. During use gases from the body and the waste start to build up inside the collection pouch and in most instances there is no way for the gas to be released except through the clamp assembly. This gas build up causes the pouch to blow up and become uncomfortable and very bulky. If the gas situation is not relieved within a reasonable time limit the waste and gas build up can be so great as to pull the pouch away from the body where it is adhered and a uncomfortable situation occurs. As a result, present day pouches and systems limit the mobility of pouch users. They become fearful of moving about because of a perceived embarrassment should a pouch be dislodged.

The desirability of fabricating an ostomy collection pouch with a valve has been recognized in U.S. Pat. No. 4,810,250, issued to Ellenberg, et al. on Mar. 7, 1989, and U.S. Pat. No. 4,863,447, issued to Smith on Sep. 5, 1989. The gas vent of Ellenberg is either fixably secured to the pouch thereof at the time of manufacture or is inserted through a pre-made opening at the time of manufacture or just prior to use by the user. No means are shown or suggested for removing the valve assembly for cleaning. As to the valve assembly disclosed in Smith, such valve assembly is removable from the pouch for cleaning but is taught to cooperate with a special fixture molded into the bag or affixed thereto at the time of manufacture. Another selectively operable vent is shown in U.S. Pat. No. 4,366,836, issued to Villari on Jan. 4, 1983. This vent is also affixed to the ostomy bag at the time of manufacture and may not be readily removed for cleaning.

Vents which cooperate with colostomy bags that are specially manufactured through communicating vents are also shown in U.S. Pat. 2,054,535 issued to A. W. Diack on Sep. 15, 1936 and in Offenlegungsschrift 25 57 66 issued to Beiersdorvorf on May 26, 1977. All of the aforementioned venting devices suffer from having to be specially accommodated for in the manufacture of a colostomy bag and additionally in some instances not being readily removable for cleaning, a distinct disadvantage since such valves are likely to fowl. Also known in the art are continuously venting gas vent filter assemblies which have the disadvantage of not only having to be manufactured with the ostomy appliances but also suffer from indiscriminate release of gases. Such devices are shown in U.S. Pat. No. 4,203,445 issued to Jessup, et al. on May 20, 1980; U.S. Pat. No. 4,211,224, issued to Kubach, et al. on Jul. 8, 1980; U.S. Pat. No. 4,411,659, issued to Jensen, et al. on Oct. 25, 1983; Offenlegungsschrift DE 3409527 issued to Beiersdorf on Sep. 19, 1985 and Offenlegungsschrift 2,307,063 issued to Virksomheder, et al. on Aug. 23, 1973.

Therefore, a primary object of the present invention is to provide a gas vent assembly for use in venting gas from the interior of the conventionally unvented ostomy collection pouch.

A further object of the present invention is to provide a method for installing a gas vent assembly for venting gas from the interior of a conventional unvented ostomy collection pouch.

A still further object of the present invention is to provide a gas vent assembly for use in venting gas from the interior of a conventional unvented ostomy collection pouch which can be easily and quickly removed from the pouch for cleaning and reinstalled therein without disrupting the use of the pouch.

Still another object of the present invention is to provide a gas vent assembly for use in venting gas from the interior of a conventional unvented ostomy collection pouch which can be installed on a conventional unvented ostomy collection pouch by the user.

Still another further object of the present invention is to provide a gas vent assembly for use in venting gas from the interior of a conventional unvented ostomy collection pouch which can be moved from the unvented pouch to another unvented pouch venting the same for continuous use.

Another further object of the present invention is to provide a gas vent assembly for ostomy collection pouches which can be selectively vented at any time, by the user and which does not release gas unless the user so desires.

Another further object of the present invention is to provide a vent for ostomy collection pouches which can simply and easily be opened and closed.

An additional object of the present invention is to provide a gas vent assembly for use in venting gas from the interior of a conventional unvented ostomy collection pouch which gives the user much more freedom and mobility then presently known to user's not restricted by travel, work, rest and recreation.

A still additional object of the present invention is to provide a gas vent assembly for use in venting gas from the interior of a conventional unvented ostomy collection pouch so that the pouch does not burst from excess gas.

A still further additional object of the present invention is to provide a gas vent assembly for use in venting gas from the interior of a conventional unvented ostomy collection pouch which provides the user peace of mind and flexibility.

An additional still further object of the present invention is to provide a gas vent assembly for use in venting gas from the interior of a conventional unvented ostomy collection pouch which is simple to design, inexpensive to manufacture, rugged in construction, easy to use, and efficient in operation.

These objects as well as further objects and advantages of the present invention will become readily apparent after reading the ensuing description of a non-limiting illustrative embodiment and reviewing the accompanying drawing.

SUMMARY OF THE INVENTION

A gas vent assembly for use in manually venting gas from the interior of a conventional unvented ostomy collection pouch, constructed in accordance with the principles of the present invention, comprises a valve assembly having an open portion, which permits gas to pass therethrough and a closed portion for preventing gas from passing therethrough. The valve assembly has an input portion for communicating with the interior of the ostomy collection pouch and an output portion for communicating with the atmosphere. A reusable mounting device for mounting the valve assembly through a selective portion of the wall of the ostomy collection pouch is provided. The portion of the wall is essentially the same of the rest of the wall of said ostomy collection pouch prior to the mounting of the valve assembly. The mounting device for releasably retaining therein a portion of the valve assembly positions the input portion of the valve assembly proximate to the interior of the ostomy collection pouch and the output portion of the valve assembly proximate the atmosphere outside of the ostomy collection pouch.

A method for providing a vent for an ostomy collection pouch, in accordance with the principles of the present invention, comprises the steps of providing a valve assembly; providing means for removably retaining the valve assembly; puncturing a hole through a selected portion of the ostomy collection pouch; inserting the valve assembly through the hole; and removably affixing the valve assembly in place with the removable retaining means.

BRIEF DESCRIPTION OF THE DRAWING

In order that the present invention may be more fully understood, it will now be described, by way of example, with reference to the accompanying drawing, in which.

DESCRIPTION OF THE PREFERRED EMBODIMENTS

Figure 1:
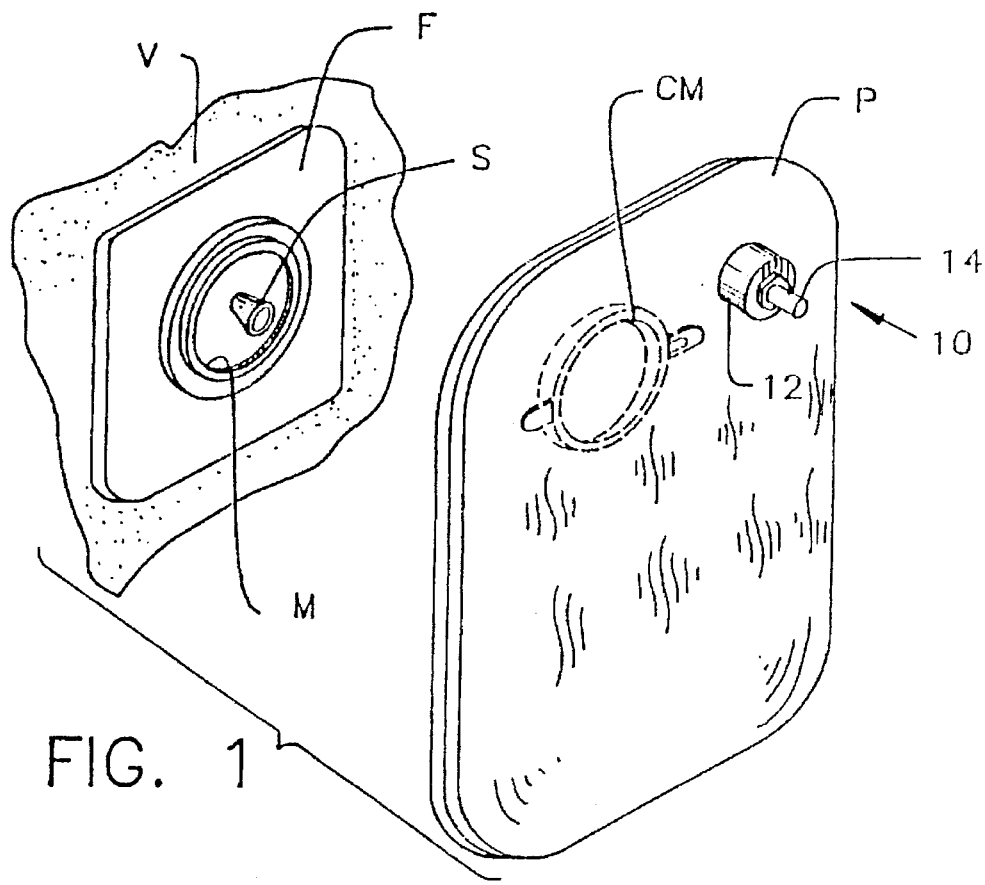
FIG. 1, is a pictorial representation of an ostomy collection pouch incorporating the principles of the present invention just prior to mounting on a cooperating flange over a patients stoma.
Figure 2:
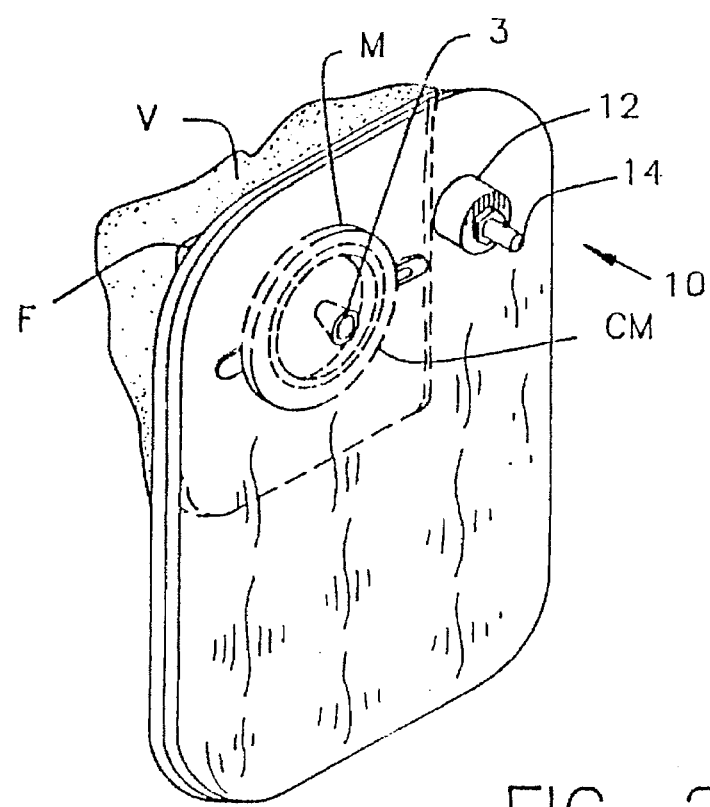
FIG. 2, is a pictorial representation of an ostomy collection pouch incorporating the principles of the present invention installed and in use.

Referring now to the figures, and more particularly, to FIGS. 1 and 2, there is illustrated a disposable or reusable ostomy collection pouch (P) having an essentially uniform wall thickness for mounting on an adhesive backed flange (F). The adhesive backed flange (F) is adhered to the skin of the user (V) in such a position that the stoma (S) of the user is surrounded by a central opening provided in the adhesive backed flange (F). The flange (F) provides a mount (M) which is adapted to cooperate with a cooperation mount (CM) disposed on the pouch (P). The pouch (P) is of a conventional unvented design and has mounted thereon a gas vent assembly 10 constructed in accordance with the principles of the present invention. The gas vent assembly 10 includes a mount 12 and a valve assembly 14 as will hereinafter be described in detail. The gas vent assembly 10 is further illustrated in FIGS. 3 and 4 of the drawing.

Figure 3:
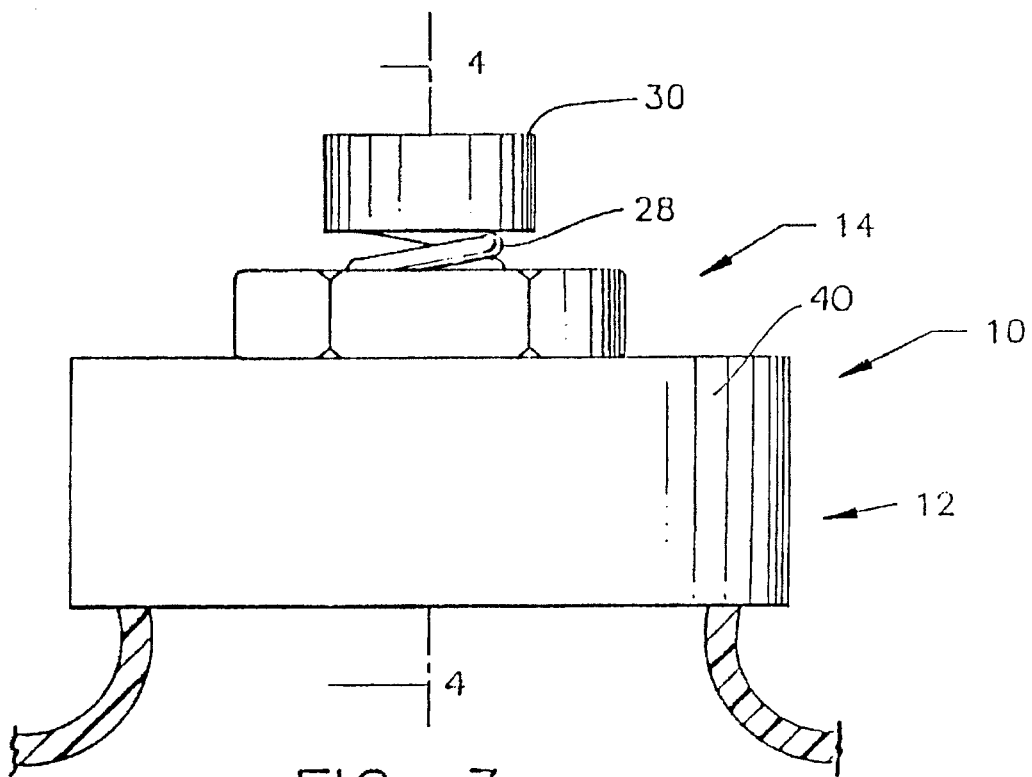
FIG. 3, is an elevational view of one embodiment of the present invention.
Figure 4:
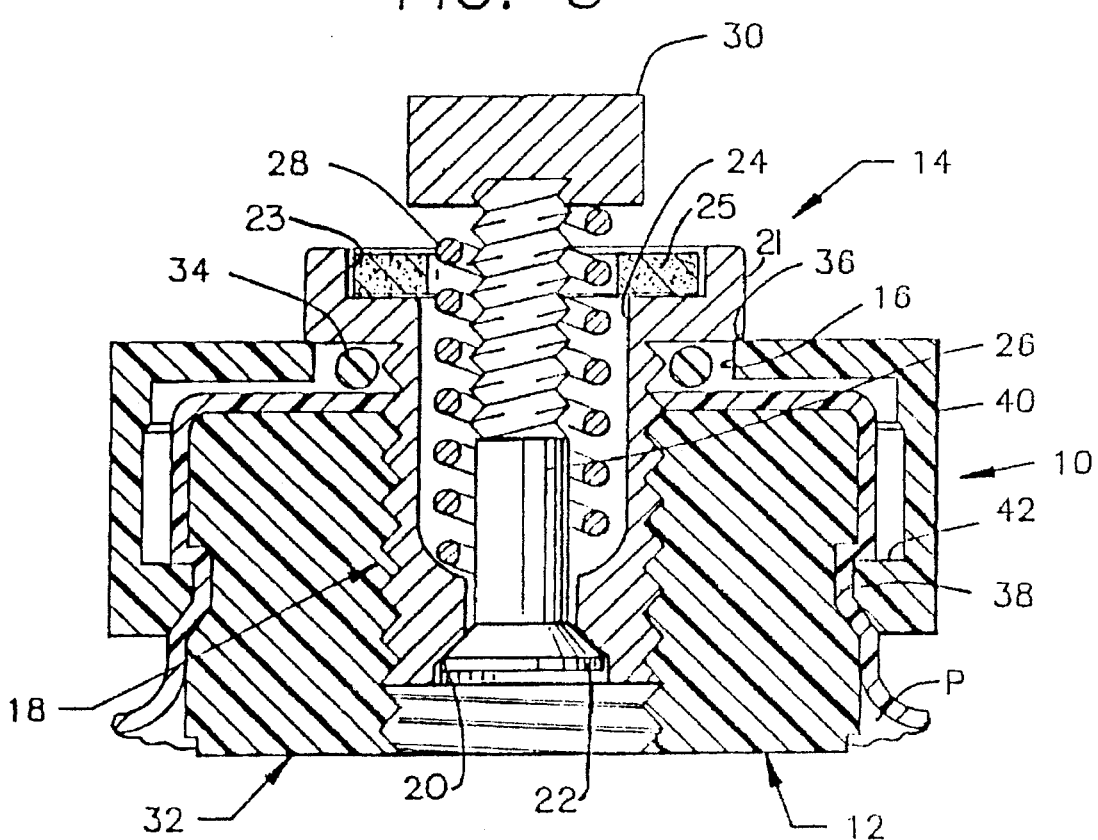
FIG. 4, is a cross-sectional view taken along the lines 4—4 of FIG. 3.

Referring now to FIGS. 3 and 4 there is shown the gas vent assembly 10 which includes a mount 12 for affixing the valve assembly 14 to a pouch (P) only a portion of which is shown. A hole 16 has been made to clear a selected portion of the wall of the pouch (P) and inserted therethrough is the valve assembly 14. The valve assembly 14 includes an externally threaded invasive portion 18 which is essentially tubular in shape and terminates in an enlarged head 21 in which is provided a reservoir 23 adapted to receive an absorbent pad 25. The pad 25 may be used for an antiseptic and/or a deodorant and has disposed therein a valve seat 20. The valve seat 20 is dimensioned to cooperate with a valve head 22 which when in contact with the valve seat 20 zero passage of gas through a longitudinal bore 24 disposed in the invasive portion 18. The valve head 22 is borne by a valve stem 26 biased in position by a spring 28. The spring 28 is biased so that it pulls the valve head 22 against the valve seat 20 when at rest. Threadably affixed to the valve stem 26 is a push button 30 which compresses the spring 28 and forces the valve head 22 away from the seat 20 by moving the valve stem 26 within the longitudinal bore 24 when pressure is applied to push button 30. When the push button is released as a result of the pressure of the spring 28 the valve head again is seated in the valve seat 20 and the longitudinal bore 24 is closed off.

The externally threaded invasive portion 18 of the valve assembly 14 is retained in position through the hole 26 in the pouch (P) by an internal retaining nut 32. The internal retaining nut 32 is threaded with threads complimentary to those on the externally threaded valve portion 18. An O-ring 34 is disposed coaxially about the longitudinal axis of the externally threaded invasive portion 18 such that when the externally threaded invasive portion 18 is threaded into the internal retaining nut 32 the O-ring forms a seal between a head flange 36 of the externally threaded invasive portion 18 and the internal retaining nut 32. The O-ring can also serve as a means for sealing the wall of the pouch (P) to the gas vent assembly 10. However, to guarantee such seal an internal retaining nut 32 has disposed therein an annular groove 38. The annular groove 38 is disposed perpendicular to the longitudinal axis of the externally threaded valve portion 18 and receives therein the wall material of the pouch (P) as illustrated. Clamping and sealing the wall of the pouch (P) in place about the gas vent assembly 10 is a cap 40, which has an internally extending annular ridge 42. When the wall of the pouch (P) is placed over the internal retaining nut 32 and the cap 40 is snapped into position so that the internally extending annular ring 42 is seated in the annular groove 38 of the internal retaining nut 32 a seal is formed between the wall of the pouch (P) and the gas vent assembly 10 effectively sealing the interior of the pouch (P) from the outside atmosphere. When the user presses on the push button 30 mounted on the valve stem 26 the valve head 22 moves away from the valve seat 20 as a result of the compression of the spring 28 and the longitudinal bore 24 of the externally threaded invasive portion 18 permits communication between the interior of the pouch and the outside atmosphere.

When the user releases the push button 30 the spring 28 acts in expansion and forces the valve stem 26 to move within the longitudinal bore 24 such that the valve head 22 of the valve stem 26 seats against the valve seat 20 sealing off communication through the longitudinal bore 24 between the outside atmosphere and the interior of the pouch (P).

It should be obvious in viewing FIG. 3 and 4 that the user can quickly and easily drop the internal retaining nut 32 into the pouch (P) form a hole in the pouch (P) to accommodate the passage of the externally threaded invasive portion 18 therethrough and thread the valve assembly 14 into the internal retaining nut 32 readying the gas vent assembly 10 for use. If desired, the valve assembly 14 can be removed for cleaning while the internal retaining nut 32 stays within the pouch and the valve assembly 14 can be returned into position through the hole 16 as desired by the user. When the useful life of the pouch (P) has been reached the valve assembly 14 and the internal retaining nut 32 can be removed by snapping off the cap 40 and unthreading the valve assembly 14 so that they can be re-used in another conventional unvented ostomy collection pouch (P) so that the gas disposed therein can be vented to the outside atmosphere.

Figure 5:
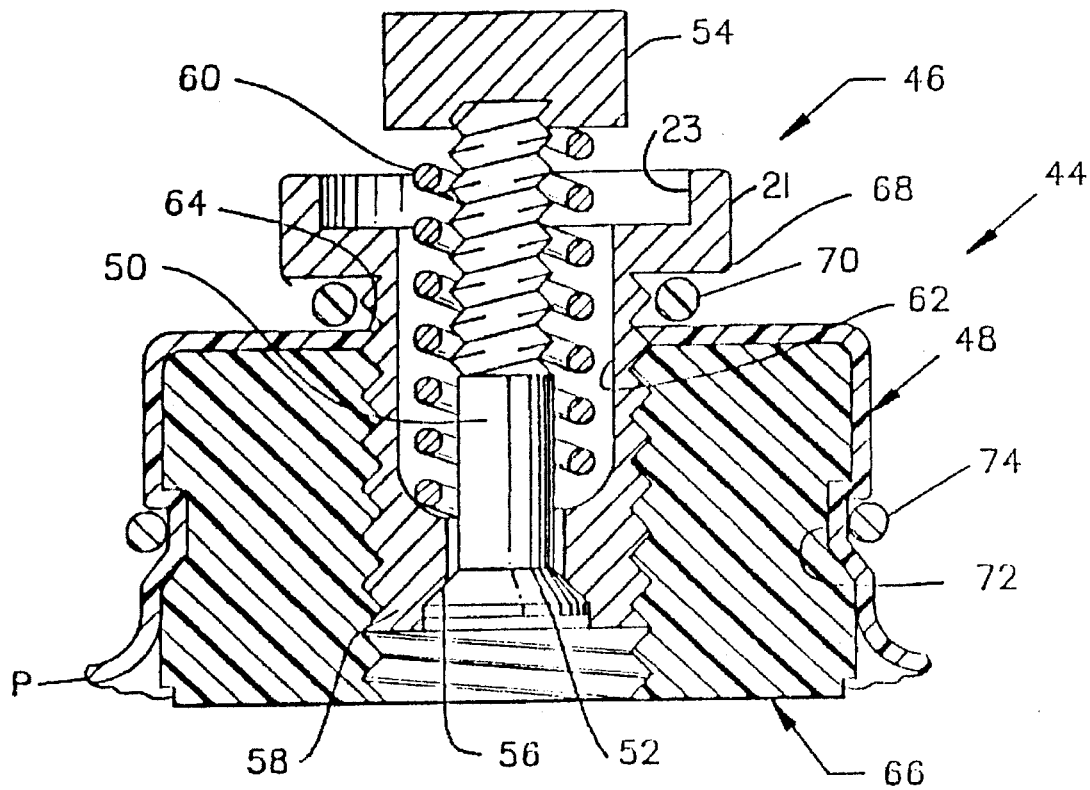
FIG. 5, is a cross-sectional view of a second embodiment of the present invention.

Referring now to FIG. 5, there is shown an alternative embodiment of the present invention. A gas vent assembly 44 includes a valve assembly 46 and a valve mount 48. The valve assembly 46 is essentially the same as the valve assembly shown in FIGS. 3 and 4 and includes a valve stem 50 bearing a valve head 52 and has a push button 54 frontally mounted on the valve stem 50. Urging the valve head 52 against the valve seat 56 disposed in an externally threaded invasive portion 58 of the valve assembly 14 is a spring 60. When the valve head 52 is seated against the valve seat 56 no gas can pass through the longitudinal bore 62 of the valve stem 50. When the push button 54 is pushed by the user the valve head 52 moves away from the valve seat 56 and gases can pass through the longitudinal bore 62 of the valve assembly 46. The externally threaded invasive portion 58 of the valve assembly 46 is held in position through a hole 64 in the wall of the pouch (P) by an internal retainer nut 66 which is internally threaded with threads that are compatible with the external threading of the externally threaded invasive portion 58 of the valve assembly 46.

Also provided to seal a head flange 68 of the externally threaded invasive portion 58 to the internal retainer nut 66 is an O-ring 70 which gets sandwiched between the internal retainer nut 66 and the head flange 68 of the valve assembly 46 when threaded. therein. A seal is created between the wall of the pouch (P) and the internal retainer nut 66 by the provision of an annular groove 72 in the internal retainer nut 66. The annular groove 72 is disposed coaxial to the longitudinal axis of the longitudinal bore 62 of the externally threaded portion 58 when the internal retainer nut 66 is disposed thereon and an O-ring 74 is provided to force the material of the wall of the pouch (P) into the annular groove 72 thereby causing an effective seal.

Figure 6:
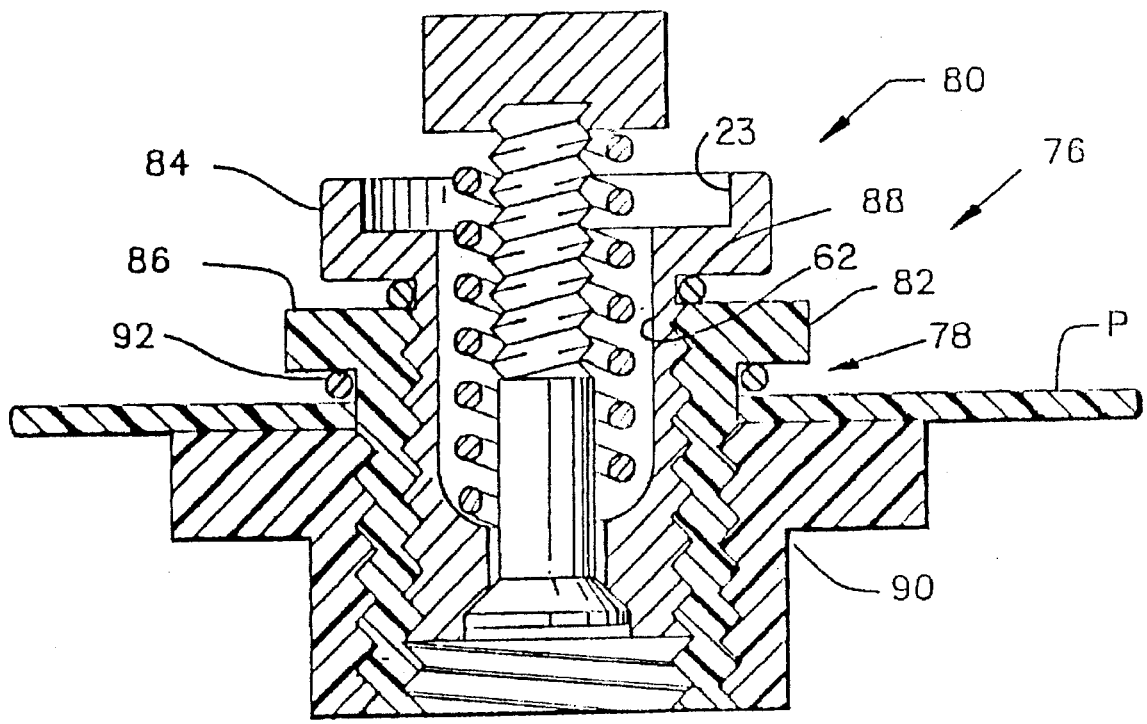
FIG. 6 is a cross-sectional view of still another embodiment of the present invention.

Referring now to FIG. 6, there is shown a gas vent assembly 76 which includes a valve mount 78 and a valve assembly 80. The valve assembly 80 is identical in form and function to the valve assemblies 46 and 14 shown, respectively, in FIGS. 5 and 4 and therefore will not be further described herein. The valve assembly 80 is threadably received in a valve fixture 82. The valve fixture 82 has a longitudinal bore 62 which is threaded to cooperate with the external threads on the valve assembly 80.

To provide a seal between the head flange 84 of the valve assembly 80 and a head flange 86 of the valve fixture 82 there is provided an O-ring 88. The O-ring 88 is compressed when the valve assembly 80 is threaded into the valve fixture 82 thereby causing a seal therebetween. The valve fixture 82 has external threads disposed on the outer surface thereof which cooperate with internal threads of an internal retainer nut 90 disposed within the pouch (P). An O-ring 92 is disposed about the external threads of the valve fixture 82 such that threading the valve fixture 82 into the internal retaining nut 90 causes compression of the O-ring between the head flange 84 and the internal retainer nut 90 so as to cause a seal therebetween and also a seal to the wall of the pouch (P) as shown in FIG. 6. This configuration of the subject invention permits fixing the internal retainer nut 90 in position so that it does not move, since it is maintained in position by the valve fixture 82 threaded therein when the valve assembly 80 is removed therefrom.

As a result the valve assembly 80 can be removed for cleaning and there is no difficulty aligning the internal retainer nut 90 with the hole disposed through the wall of the pouch (P) to accommodate the mounting of the gas vent assembly 76 therethrough. Therefore, the valve assembly 80 can be removed for cleaning with minimal effort.

Figure 7:
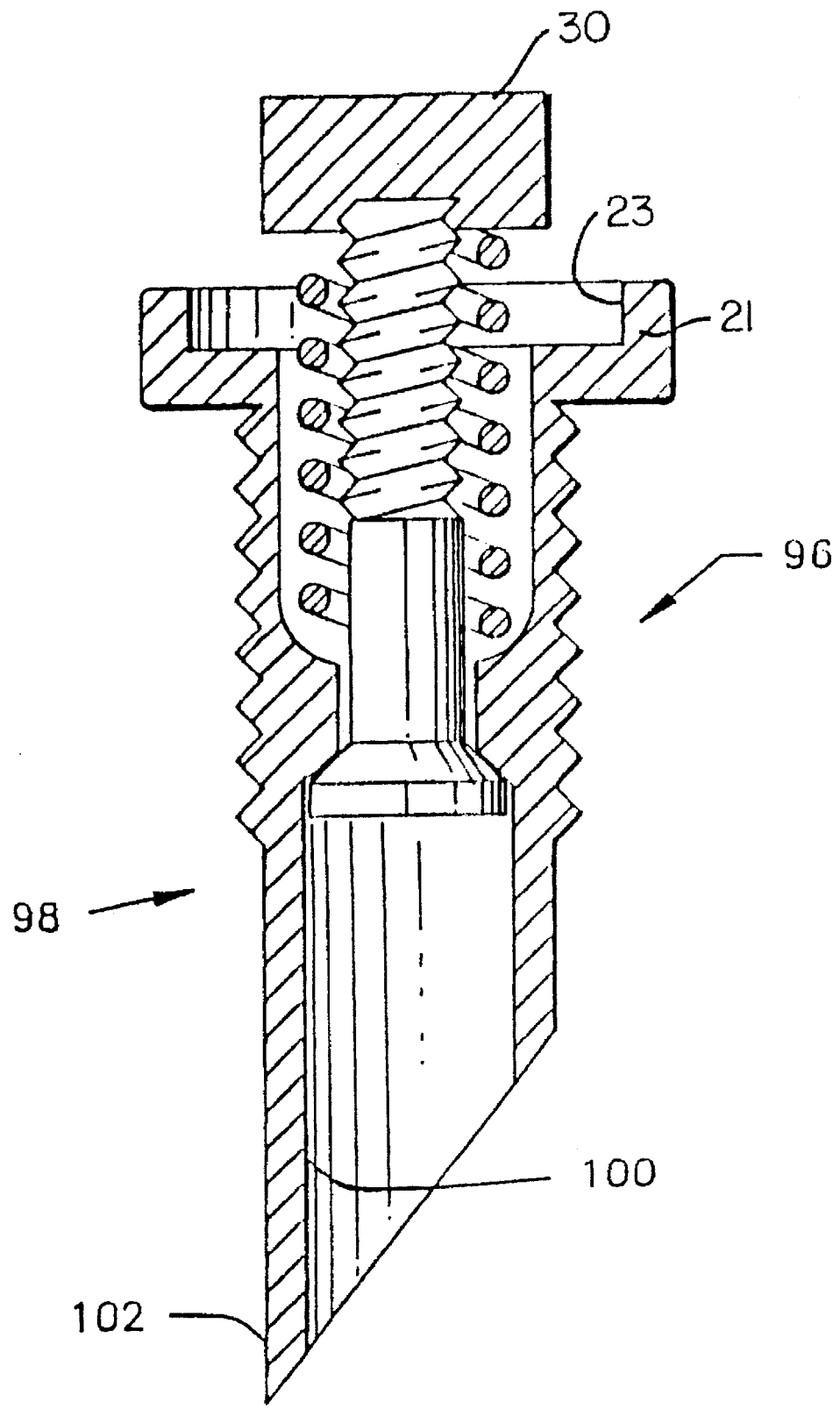
FIG. 7 is a cross-sectional view of a self-piercing valve assembly constructed in accordance with the principles of the present invention.

The one issue which has not been heretofore addressed is how a hole is made in the wall of the pouch (P). This can be made in any convenient manner and can be a rough punched through hole made with a sharp instrument, if desired, since in each configuration as previously described the ultimate seal is made at a point remote to the actual hole. One possibly more elegant method to make the hole is through employment of a self-piercing valve assembly 96 as illustrated in FIG. 7. The self-piercing valve assembly 96 is essentially the same as the valve assemblies 80, 46, and 14, previously discussed, but also includes a forward piercing portion 98 that has a longitudinal chamber 100 disposed therethrough. The edge 102 of the piercing element 98 of the valve assembly 96 easily and quickly pierces a hole through the wall of the pouch (P) when the valve assembly 96 is threaded into a valve fixture 82 such as illustrated in FIG. 6 or an internal retainer nut 32 or 66.

In operation, the various embodiments of the venting valve may readily be affixed to a conventional unvented ostomy bag and attached to a user thereof who may vent the bag whenever he chooses in order to avoid failure of the bag and thereby avoid embarrassment.

Hereinbefore has been disclosed a reliable, reusable ostomy bag valve that can be selectively activated and affixed to an unvented bag. It will be understood that various changes in the details, materials, arrangement of parts and operation of conditions which have been herein described and illustrated in order to explain the nature of the invention may be made by those skilled in the art within the principles and scope of the invention.

We claim:

1. A manual gas venting assembly for use in venting gas from the interior of a conventional essentially uniform unvented ostomy collection pouch to the atmosphere comprising:

A. a manually operable valve assembly having an open position, which permits gas to pass therethrough from the interior of an ostomy collection pouch to the atmosphere, and a normally closed position for preventing gas from passing therethrough, having;
   a) an input portion for communicating with the interior of the ostomy collection pouch,
   b) an output portion for communicating with the atmosphere, and
   c) reusable mounting means for mounting said valve assembly to the ostomy collection pouch to provide access to the interior thereof, said mounting means releasably retaining therein a portion of said manually operable valve assembly so as to position said valve assembly input portion proximate a stoma of a user, said mounting means including;
      i) a valve mount for receiving therein said input portion of said valve assembly, said valve mount having an invasive portion for extending through said ostomy collection pouch providing access to said interior thereof;
      ii) an internal retainer to be disposed in said interior of said ostomy collection pouch, said internal retainer adapted to removably receive therein said invasive portion of said valve mount,
      iii) means for removably securing said invasive portion of said valve mount to said internal retainer, and
      iv) means for sealing a portion of said ostomy pouch between said internal retainer and said valve mount; and
B. means for piercing and puncturing a hole through the ostomy collection pouch to provide access to the interior thereof and to permit the insertion of said valve assembly therethrough, said piercing means being part of said input portion of said valve assembly.

2. A manual gas venting assembly in accordance with claim 1, wherein said input portion of said valve assembly bears said piercing and puncturing means, said piercing and puncturing means includes a sharpened extensive tubular portion integral with said input portion of said valve assembly.

3. A manual gas venting assembly in accordance with claim 1, wherein said removable securing means comprises an internally threaded opening disposed in said internal retainer and complementary external threads disposed about said valve mount.

4. A manual gas venting assembly in accordance with claim 1, wherein said sealing means comprises an annular flange provided by said valve mount, and an O-ring disposed about said invasive portion thereof, wherein threading of said valve mount into said internal retainer compresses said O-ring between said annular flange and said internal retainer thereby creating a seal with said portion of said ostomy pouch.

5. A manual gas venting assembly in accordance with claim 1, wherein said valve assembly comprises threads on said input portion thereof and said valve mount comprises complementing internal threads in the portion thereof which receives said input portion of said valve assembly, said valve assembly further includes an O-ring disposed about said threads on said input portion thereof, wherein threading of said valve assembly into said valve mount compresses said O-ring and seals said valve assembly to said valve mount.

6. A manual gas venting assembly for use in venting gas from the interior of a conventional unvented ostomy collection pouch to the atmosphere comprising:

A. a manually operable valve assembly having an open position, which permits gas to pass therethrough from the interior of an ostomy collection pouch to the atmosphere, and a normally closed position for preventing gas from passing therethrough, having;
   a) an input portion for communicating with the interior of the ostomy collection pouch,
   b) an output portion for communicating with the atmosphere, and
   c) reusable mounting means for mounting said valve assembly to the ostomy collection pouch to provide access to the interior thereof, said mounting means releasably retaining therein a portion of said manually operable valve assembly so as to position said valve assembly input portion proximate a stoma of a user, said mounting means including;
      i) a valve mount for receiving therein said input portion of said valve assembly, said valve mount having an invasive portion for extending through the ostomy collection pouch providing access to the interior thereof,
      ii) an internal retainer to be disposed in the interior of the ostomy collection pouch, said internal retainer adapted to removably receive therein said invasive portion of said valve mount,
      iii) means for removably securing said invasive portion of said valve mount to said internal retainer, and
      iv) means for sealing a portion of the ostomy collection pouch between said internal retainer and said valve mount; and
B. means for piercing and puncturing a hole through the ostomy collection pouch to provide access to the interior thereof and to permit the insertion of said valve assembly therethrough, said piercing means being part of said input portion of said valve assembly.

7. A manual gas venting assembly in accordance with claim 6, wherein said removable securing means comprises an internally threaded opening disposed in said internal retainer and complementary external threads disposed about said valve mount.

8. A manual gas venting assembly in accordance with claim 6, wherein said sealing means comprises an annular flange provided by said valve mount, and an O-ring disposed about said invasive portion thereof, wherein threading of said valve mount into said internal retainer compresses said O-ring between said annular flange and said internal retainer thereby creating a seal with said portion of said ostomy pouch.

9. A manual gas venting assembly in accordance with claim 6, wherein said valve assembly comprises threads on said input portion thereof and said valve mount comprises complementing internal threads in the portion thereof which receives said input portion of said valve assembly, said valve assembly further includes an O-ring disposed about said threads on said input portion thereof, wherein threading of said valve assembly into said valve mount compresses said O-ring and seals said valve assembly to said valve mount.

10. A manual gas venting assembly for use in venting gas from the interior of a conventional essentially uniform unvented ostomy collection pouch to the atmosphere comprising:

A. a manually operable valve assembly having an open position, which permits gas to pass therethrough from the interior of an ostomy collection pouch to the atmosphere, and a normally closed position for preventing gas from passing therethrough, having;

a) an input portion for communicating with an ostomy collection pouch, said input portion having piercing and puncturing means disposed thereon including a sharpened extensive tubular portion integral with said input portion of said valve assembly, b) an output portion for communicating with the atmosphere, and c) mounting means for mounting said valve assembly to the ostomy collection pouch to provide access to the interior thereof, said mounting means including:

i) a valve mount for receiving therein said input portion of said valve assembly, said valve mount having an invasive portion for extending through the ostomy collection pouch providing access to the interior thereof, ii) an internal retainer to be disposed in the interior of the ostomy collection pouch, said internal retainer adapted to removably receive therein said invasive portion of said valve mount, iii) means for removably securing said invasive portion of said valve mount to said internal retainer; and iv) means for sealing a portion of the ostomy collection pouch between said internal retainer and said valve mount; said mounting means releasably retaining therein a portion of said manually operable valve assembly so as to position said input portion thereof proximate a stoma of a user.

11. A conventional unvented ostomy collection pouch and a manual gas venting assembly for use in venting gas from the interior of said conventional unvented ostomy collection pouch to the atmosphere comprising:

A. an ostomy collection pouch, said pouch being essentially uniform prior to the mounting of a valve assembly;

B. a manually operable valve assembly having an open position, which permits gas to pass therethrough from the interior of said ostomy collection pouch to the atmosphere, and a normally closed position for preventing gas from passing therethrough, having;

a) an input portion for communicating with the interior of said ostomy collection pouch, said input portion having piercing and puncturing means disposed thereon including a sharpened extensive tubular portion integral with said input portion of said valve assembly, b) an output portion for communicating with the atmosphere, and c) mounting means for mounting said valve assembly to said ostomy collection pouch to provide access to said interior thereof, said mounting means including:

i) a valve mount for receiving therein said input portion of said valve assembly, said valve mount having an invasive portion for extending through said ostomy collection pouch providing access to said interior thereof, ii) an internal retainer disposed in said interior of said ostomy collection pouch, said internal retainer adapted to removably receive therein said invasive portion of said valve mount, iii) means for removably securing said invasive portion of said valve mount to said internal retainer; and iv) means for sealing a portion of said ostomy collection pouch between said internal retainer and said valve mount;

whereby, said mounting means releasably retains therein a portion of said manually operable valve assembly so as to position said input portion thereof proximate a stoma of a user.

\* \* \* \* \*